US008895259B2

(12) United States Patent
Rechner

(10) Patent No.: US 8,895,259 B2
(45) Date of Patent: Nov. 25, 2014

(54) METHOD FOR DETERMINATION OF PLATELET FUNCTION UNDER FLOW CONDITIONS

(75) Inventor: Andreas Rechner, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 1199 days.

(21) Appl. No.: 11/790,607

(22) Filed: Apr. 26, 2007

(65) Prior Publication Data

US 2007/0254324 A1    Nov. 1, 2007

(30) Foreign Application Priority Data

Apr. 28, 2006  (DE) .......................... 10 2006 020 386

(51) Int. Cl.
*C12Q 1/56* (2006.01)
*C12Q 1/00* (2006.01)
*G01N 33/86* (2006.01)

(52) U.S. Cl.
CPC ..................................... *G01N 33/86* (2013.01)
USPC ................. 435/13; 435/4; 435/7.92; 435/7.1; 435/7.5; 435/7.93

(58) Field of Classification Search
None
See application file for complete search history.

(56) References Cited

U.S. PATENT DOCUMENTS

| 5,051,239 | A |   | 9/1991 | von der Goltz |        |
|-----------|---|---|--------|---------------|--------|
| 5,622,867 | A | * | 4/1997 | Livesey et al.| 436/18 |
| 6,702,987 | B1| * | 3/2004 | Kundu et al.  | 422/58 |
| 2007/0254325 | A1 |   | 11/2007 | Rechner |        |

FOREIGN PATENT DOCUMENTS

| EP | 0716744 B1 | 11/2001 |
| JP | 57-000552 A | 1/1982 |
| JP | 1-201157 A | 8/1989 |
| JP | 9-502532 A | 3/1997 |
| WO | WO 96/00898 A1 | 1/1996 |
| WO | WO 97/34698 A1 | 9/1997 |
| WO | WO 02/074322 A2 | 9/2002 |
| WO | WO 2005/007868 A2 | 1/2005 |

OTHER PUBLICATIONS

European Search Report for European Patent Application No. 07007504.9 (Jul. 7, 2006).
Mischke, R., et al., "Influence of Platelet Count, Acetylsalicylic Acid, von Willebrand's Disease, Coagulopathies, and Haematocrit on Results Obtained Using a Platelet Function Analyser in Dogs," Vet. J., 165:43-53 (2003).
Xu, B., et al., "Acyclic Analogues of Adenosine Biphosphates as P2Y Receptor Antagonists: Phosphate Substitution Leads to Multiple Pathways of Inhibition of Platelet Aggregation," J. Med. Chem., 45:5694-5709 (2002).
Sigma-Aldrich Catalog Description for Product No. M5942, "MRS2395 Cell Signaling and Neuroscience First P2Y12 Receptor Antagonist Available from Sigma-RBI," downloaded from the Sigma-Aldrich website on Jun. 12, 2007.
Judge, H.M., et al., "Incomplete P2Y12 Receptor Blockade by Clopidogrel is Not Due to the Presence of an Internal Pool of P2Y12 Receptors," J. Thromb. Haemost., 3(suppl 1):abstract (2005).
Wiviott, S.D., "Randomized Comparison of Prasugrel (CS-747, LY640315), a Novel Thienopyridine P2Y12 Antagonist, With Clopidogrel in Percutaneous Coronary Intervention: Results of the Joint Utilization of Medications to Block Platelets Optimally (JUMBO)-TIMI 26 Trial," Circulation, 111(25):3366-3373 (2005).
Kam, P.C.A., et al., "The Thienopyridine Derivatives (Platelet Adenosine Diphosphate Receptor Antagonists), Pharmacology and Clinical Developments," Anaesthesia, 58:28-35 (2003).
Kozek-Langenecker, S.A., et al., "[Locoregional Anaesthesia and Coagulation Inhibitors. Recommendations of the Task Force on Perioperative Coagulation of the Austrian Society for Anesthesiology and Intensive Care Medicine]," Anaesthesist, 54:5:476-84 (2005).
André, P., et al., "Anticoagulants (Thrombin Inhibitors) and Aspirin Synergize With $P2Y_{12}$ Receptor Antagonism in Thrombosis," Circulation, 108(21):2697-2703 (2003).
Houston, D., et al., "[$^{32}$P]2-iodo-$N^6$-methyl-($N$)-methanocarba-2'-deoxyadenosine-3',5'-bisphosphate ([$^{32}$P]MRS2500), a Novel Radioligand for Quantification of Native $P2Y_1$ Receptors," Br. J. Pharmacol., 147:459-67 (2006).
Jin, J., et al., "Adenosine Diphosphate (ADP)-induced Thromboxane $A_2$ Generation in Human Platelets Requires Coordinated Signaling Through Integrin $\alpha_{IIb}\beta_3$ and ADP Receptors," Blood, 99(1):193-98 (2002).
Miyamoto, K. et al., "Stimulatory and Inhibitory Effects of Forskolin on Adenylate Cyclase in Rat Normal Hepatocytes and Hepatoma Cells," J. Pharmacobio-Dyn., 12:87-93 (1989).
Malinin, A. et al., "Monitoring platelet inhibition after clopidogrel with the VerifyNow-P2Y12® rapid analyzer: The VERIfy Thrombosis risk ASsessment (VERITAS) study," Thrombosis Research, 119(3):277-84, (2007) (Epub Mar. 24, 2006).
Coleman B., "Platelet inhibition monitoring implications for POCT," Oral Presentation of Feb. 8, 2006, Internet document, address: www.pointofcare.net/NewYork/Feb82006Meeting.htm.
Fattorutto M., "Evaluation of platelet aggregation in flow and platelet aggregometry during pregnancy," Br J Anaesth., 90(2):252 (2003).
Harrison P. et al., "Screening for aspirin responsiveness after transient ischemic attack and stroke," Stroke, 36(5):1001-5 (2005).
Lordkipanidzé M. et al., "Comparison of four tests to assess inhibition of platelet function by clopidogrel in stable coronary artery disease patients," Eur Heart J., 29(23):2877-85 (2008).
Rand M.L. et al., "Platelet function assays," Transfus Apher Sci., 28(3):307-17 (2003).
Vincelot A. et al., "Platelet function during pregnancy: an evaluation using the PFA-100 analyser," Br J Anaesth., 87(6):890-3 (2001).

* cited by examiner

*Primary Examiner* — Lisa J Hobbs
(74) *Attorney, Agent, or Firm* — Finnegan, Henderson, Farabow, Garrett & Dunner, LLP

(57) ABSTRACT

The invention lies in the area of platelet function diagnostics and relates to an in vitro method for the determination of platelet function under flow conditions. The method is particularly suitable for the determination of the effect of clopidogrel after oral intake and of other P2Y(12) antagonists with antithrombotic activity as well as the determination of P2Y(1) receptor antagonists with antithrombotic activity.

7 Claims, 3 Drawing Sheets

METHOD FOR DETERMINATION OF PLATELET FUNCTION UNDER FLOW CONDITIONS

This application claims the benefit of priority under 35 U.S.C. §119 to German Patent Application No. DE 10 2006 020 386.0, filed on Apr. 28, 2006, incorporated herein by reference.

The invention lies in the area of platelet function diagnostics and relates to an in vitro method for the determination of platelet function under flow conditions. The method is particularly suitable for the determination of the effect of clopidogrel after oral intake and of other P2Y(12) antagonists with antithrombotic activity and for the determination of P2Y(1) receptor antagonists with antithrombotic activity.

Physiological processes that on the one hand guarantee the fluidity of blood in the vascular system and on the other avoid extravascular blood loss through the formation of blood clots are classified under the term hemostasis. Numerous protein factors are involved in the regulation of hemostasis as well as also cellular components, for example thrombocytes (platelets). In the case of vessel damage attachment of platelets to the subendothelial collagen first takes place. This adhesion is mediated by adhesion proteins such as the von Willebrand factor (VWF). During the adhesion process the platelets are activated and release mediators from their granulae through which the aggregation of further platelets and an increase in activation are induced. In this way primary vessel wall occlusion (primary hemostasis) takes place which then is further stabilized by reactions of the plasmatic coagulation system (secondary hemostasis). Dysregulation of these processes can lead to thrombophilia or a tendency towards hemorrhage, which dependent upon the degree of severity can have life-threatening consequences.

Different in vitro test methods have been developed in coagulation diagnostics, with the help of which it is possible to determine whether the blood of a patient coagulates properly or whether a coagulation defect is present. In the case of a coagulation defect it is frequently necessary to obtain precise information on the cause of the defect present in order to be able to select the optimal therapeutic measures. An important sub-function of the coagulation system that can be investigated specifically is primary hemostasis, which is essentially dependent on the functionality of the platelets.

Methods to determine platelet function are not only used for the diagnosis of acquired or inherited platelet dysfunction, but also for monitoring antithrombotic therapies. Medication that inhibits the aggregation of platelets is used mainly for the prophylaxis and therapy of arterial thromboembolitic events such as myocardial infarction or stroke. The most widely used active compounds with platelet aggregation inhibitory activity are acetylsalicylic acid (ASA) and the thienopyridines clopidogrel and ticlopidine. ASA irreversibly inhibits cyclooxygenase-1 (COX-1), an intracellular enzyme that is involved in the synthesis of the platelet aggregation promoter thromboxane A2. Owing to their mode of activity clopidogrel and ticlopidine belong to the class of P2Y(12) antagonists. After oral intake of clopidogrel or ticlopidine metabolites are formed in the liver that block selectively the purinergic P2Y(12) receptor. The purinergic P2Y(12) receptor is expressed on the platelet surface and can be activated by extracellular adenosine-5'-diphosphate (ADP). As a consequence of the activation of the P2Y(12) receptor intracellular processes are induced in the platelets, for example the inhibition of the formation of cAMP, that give rise to a platelet aggregation reaction. P2Y(12) antagonists block the P2Y(12) receptors on the platelet surface and thus possess antithrombotic activity.

The second purinergic ADP receptor P2Y(1) is also expressed on the platelet surface and is activated by extracellular adenosine-5'-diphosphate.

As a consequence of the activation of the purinergic P2Y(1) receptor intracellular processes are initiated in the platelets, for example an increase in intracellular calcium, that give rise to a platelet aggregation reaction. P2Y(1) receptor antagonists act against this process and thus have antithrombotic activity.

Precise knowledge of the status of the platelet function of patients who are receiving antithrombotic therapy is considered to be increasingly important since, for example, the occurrence of so-called clopidogrel resistance is under serious consideration as an increasing risk factor. Clopidogrel resistance is present when the platelet function of a patient is only slightly influenced by the administration of a standard dose of clopidogrel, or not at all. On the one hand a test can be carried out to determine whether an adequate antithrombotic response is actually achieved with a selected dose by determination of platelet function. On the other hand, doses or responses of an antithrombotic medication that are too high can be determined and treated, which is necessary, for example, prior to surgery in order to exclude bleeding complications.

Different methods for the investigation of platelet function are known in the prior art. Bleeding time determination is a global in vivo test which records primary hemostasis. The bleeding time is determined wherein the patient is given a small cut or prick injury and the time for coagulation is measured. It is a poorly standardizable, coarsely informative test that is used primarily in an emergency situation in order to obtain an overview of primary hemostasis. Taking platelet aggregation inhibitors leads to an increase in bleeding time. The disadvantage of bleeding time determination is that platelet dysfunction cannot be excluded even with a normal bleeding time.

Different in vitro methods allow a significantly more sensitive detection of platelet dysfunction to be made. Normally in these methods the platelet aggregation is induced in a whole blood sample or in a sample of platelet-rich plasma (PRP) by the addition of an activator and the aggregation reaction is measured. The most commonly used activators used for the induction of platelet activation are ADP (adenosine 5'-diphosphate), collagen, epinephrine (adrenaline), ristocetin and different combinations thereof as well as thrombin, TRAP (thrombin receptor activating protein) or serotonin.

In light transmission aggregometry, also known as Born platelet aggregation, the aggregation efficiency of platelets in platelet-rich plasma is measured photometrically in the presence of aggregation-inducing compounds in an aggregometer. The light transmission of the PRP sample is increased due to aggregate formation so that the rate of aggregate formation, for example, can be determined by measurement of the light transmission. The therapeutic effects of platelet aggregation inhibitors used medically can also be determined with the aid of light transmission aggregometry. A disadvantage of light transmission aggregometry is that only platelet-rich plasma can be used as sample material. Platelet-rich plasma lacks not only important blood components such as, for example, red and white blood cells, but also requires a time-consuming and error-prone sample preparation.

Another test principle for the determination of platelet function is realized in the Platelet Function Analyzer (PFA- 100®, Dade Behring Marburg GmbH, Marburg, Germany). The PFA-100® is a global, automated and standardized in vitro whole blood test with which primary hemostasis is measured under flow conditions and thus in the presence of high shear forces. In order to simulate the flow conditions and the shear forces that prevail in smaller arterial blood vessels a partial vacuum of about −40 mbar is produced in a special test cartridge. The citrated whole blood that is located in a sample reservoir is sucked through a capillary with a diameter of about 200 µm. The capillary leads into a measurement chamber which is closed with a partition member, for example a membrane, which has a central capillary opening (aperture) through which the blood flows due to the partial vacuum. In most cases the membrane, at least within the region surrounding the aperture, is coated with one or more activators that induce platelet aggregation so that the passing blood comes into contact with the aggregation-inducing substances in the region of the aperture. As a consequence of the induced adhesion and aggregation of the platelets a thrombus is formed in the region of the aperture which seals the membrane opening and stops the blood flow. In this system the time required to close the membrane opening is measured. This so-called closure time correlates with the functional efficiency of the platelets. A test cartridge for use in a method for the determination of platelet function based on the closure time is described, for example, in patent specification WO 97/34698. Thus far test cartridges that are equipped with a membrane that is coated with collagen (Col) and also with either ADP or epinephrine (Epi) are used in the method for the determination of closure time. Subject to the construction, a distinction is thus made between Col/ADP test cartridges and Col/Epi test cartridges. Normally a patient sample is first analyzed with the aid of a Col/Epi test cartridge. In the case of an abnormally increased Col/Epi closure time, which indicates a disorder of platelet aggregation, a Col/ADP measurement is subsequently carried out. If the Col/ADP closure time is likewise abnormally increased this is an indicator of platelet dysfunction or a disorder of the von Willebrand factor. If in contrast the Col/ADP closure time is normal this can indicate the presence of acetylsalicylic acid or the presence of an acquired or inherited thrombocytopathy such as, for example, storage pool disease. A disadvantage of the PFA-100® system is that the available Col/ADP and Col/Epi test cartridges have only a limited sensitivity for the aggregation inhibitory effect of platelet aggregation inhibitors of the thienopyridine group (e.g. clopidogrel, ticlopidine). A more reliable determination of the therapeutic effect of the medically used clopidogrel and ticlopidine, especially when the patient has also taken ASA (e.g. Aspirin®) is hitherto not possible with the help of the known Col/ADP and Col/Epi test cartridges in the PFA-100® system.

The patent specification WO 2005/007868 A2 describes an alternative method for the determination of platelet function that allows the detection of the therapeutic effect of clopidogrel and other P2Y(12) antagonists. In this method a whole blood sample of a patient is mixed with an anticoagulant and treated with ADP for the induction of platelet aggregation. In addition, prostaglandin E1 (PGE 1) is added to the sample. Prostaglandin E1, a product of human arachidonic acid metabolism, is able to reduce the reactivity of platelets significantly, even in low doses, and is therefore also used for the inhibition of platelet activation. In the test method described in WO 2005/007868 A2, PGE 1 is used to reduce the undesirable activation of the ADP receptor P2Y(1) and thus to increase the specificity of the test method for the P2Y(12) receptor and for P2Y(12) antagonists such as clopidogrel. In addition, microparticles to which a ligand for the GPIIb/IIIa receptor such as, for example, fibrinogen is coupled are added and the aggregation reaction is measured aggregometrically on the basis of the increasing light transmission. A disadvantage of the previously described method is that as with light transmission aggregometry platelet function is not determined under the influence of flow conditions and shear forces.

SUMMARY OF THE INVENTION

The object forming the basis of the present invention is to provide a sensitive method for the determination of platelet function under flow conditions that allows in particular the determination of the antithrombotic effect of P2Y(12) antagonists. The solution to the object lies in the provision of the methods according to the invention described in the claims.

The object of the present invention is an in vitro method for the determination of platelet function in a whole blood sample. Preferably the whole blood sample is freshly drawn anticoagulated venous human or animal blood that is to be investigated within four hours after blood collection with the help of the method according to the invention. The whole blood is preferably anticoagulated by the addition of an anticoagulant. Suitable for use as anticoagulant are buffered calcium-binding citrate solutions such as, for example, 3.2 or 3.8% buffered sodium citrate solutions, as well as natural or synthetic direct thrombin inhibitors such as, for example, hirudin, PPACK (D-Phe-Pro-Arg-chloromethyl ketone, HCl), argatroban and melagatran, or natural or synthetic direct Factor Xa inhibitors such as, for example, antistasin, tick anticoagulant peptide, yagin, draculin, GGACK (H-Glu-Glu-Arg-chloromethyl ketone), diamidino-Factor Xa inhibitors and monobenzamidine Factor Xa inhibitors.

DETAILED DESCRIPTION OF THE INVENTION

The method according to the invention for the determination of platelet function comprises several methodological steps. For the simulation of the physiological flow conditions prevailing in small arteries the blood that is initially located in a reservoir is passed though a capillary that preferably has a diameter of about 200 µm. The capillary leads into a measurement chamber that is separated into two compartments by a partition member. The partition member has an opening through which the blood is passed from the first into the second compartment. The partition member comprises at least one platelet activator whereby the blood flowing through the opening of the partition member is brought into contact with this at least one platelet activator contained in or on the partition member. As a result of the platelet aggregation that is induced by the contact with the at least one platelet activator a thrombus forms at the opening of the partition member. The time that is necessary for the formation of the thrombus at the opening of the partition member up to closure of the opening is measured.

Preferably the closure time is measured in that an apparatus is used that comprises a pressure sensor which determines the blood flow through the aperture during the test. Thus, after initial rapid aspiration of the dead volume of the test cartridge the initial flow rate is first determined. If the flow rate falls below 10% of this initial flow rate for more than 3 seconds the measurement is ended and the time passed until then is recorded as the so-called closure time. This so-called closure time, which is i.a. dependent on the aggregation reaction of the stimulated platelets, is a measure of platelet function. Preferably the closure time that was measured for a whole blood sample of a patient is compared with a closure time reference range for whole blood samples of healthy subjects.

Preferably the blood flow through the capillary and through the opening of the partition member is produced by creating a partial vacuum in the measurement chamber, that is by suction. In a particularly preferred embodiment the partial vacuum is produced by the combined action of a suitable test cartridge and an apparatus. An example of such a system is described, for example, in patent specification WO 97/034698.

The method according to the invention is distinguished in that, before passing through the capillary, the whole blood sample is mixed with at least one activator of intracellular adenylate cyclases, such as, for example, with prostaglandin E1 (PGE1) and/or with forskolin and/or prostaglandin I2 (synonym: prostacycline) and/or derivatives or analogs thereof. Preferred prostaglandin I2 analogs are iloprost and cicaprost. Prostaglandin E1 is added to the whole blood sample preferably in a final concentration of from 1 nM to 50 nM, particularly preferably in a final concentration of from 10 nM to 20 nM, very particularly preferably in a final concentration of from 11 nM to 13 nM. Forskolin is added to the whole blood sample preferably in a final concentration of from 0.1 µM to 5 µM, particularly preferably from 0.5 µM to 2.5 µM, very particularly preferably from 1 µM to 1.5 µM.

The whole blood sample can be mixed with the desired activator by simple mixing with a solution which comprises at least one activator of intracellular adenylate cyclases. For this purpose, the at least one activator of intracellular adenylate cyclases can for example either already be present in the withdrawal medium which additionally comprises an anticoagulant, or the solution is added to the whole blood which has already been anticoagulated. It is further possible for the at least one activator of intracellular adenylate cyclases to be present in the reservoir of the device provided for the determination of the closure time of the sample. The at least one activator of intracellular adenylate cyclases can be introduced into the reservoir either in lyophilized or in dissolved form.

The partition member used in the method according to the invention comprises at least one platelet activator for inducing platelet aggregation. The partition member used can comprise for example a platelet activator from the group of purinergic receptor activators, which includes in particular adenosine 5'-diphosphate (ADP) and 2-methylthioadenosine 5'-diphosphate (2-MeSADP) and derivatives thereof. In a preferred embodiment, the partition member used comprises an ADP salt or a 2-MeSADP salt. In a preferred embodiment, the partition member used comprises from 1 to 100 µg, particularly preferably 10 to 50 µg, of ADP. The partition member used may further comprise a platelet activator from the group of collagen and epinephrine, so that 0.1-5 µg, particularly preferably 1 µg of collagen, or 1-100 µg of epinephrine are used. In other preferred embodiments, partition members which comprise ADP and collagen or epinephrine and collagen are used. Partition members of this type and their preparation and use are described for example in the patent specification EP 716 744 B1.

In a further preferred embodiment of the method according to the invention a partition member is used that also comprises calcium ions, preferably in the form of calcium chloride dihydrate. In a preferred embodiment a partition member is used that comprises 50 to 200 µg, especially preferred 100 to 150 µg, most especially preferred 125 µg calcium ions in the form of calcium chloride dihydrate.

The partition member used is a porous or nonporous support matrix for the at least one platelet activator for inducing platelet aggregation and, where appropriate, for calcium ions. Preferably the partition member is constructed in the form of a membrane. The preferred material is liquid-absorbing so that the aforementioned substances can be applied in solution. Especially preferred materials are cellulose esters, ceramic, nylon, polypropylene, polyether sulfone, and polyvinylidene fluoride (PVDF). Preferably the partition member wetted or soaked with the desired substances is dried. By contact of the blood with the partition member the substances are dissolved from the partition member and mixed with the blood sample.

It has been found that on use of a partition member which comprises at least one platelet activator from the group of purinergic receptor activators such as, for example, ADP (see also table 2) in the method according to the invention, the platelet aggregation-inhibiting activity of acetylsalicylic acid (ASA) can be minimized to such an extent that precise determination of the platelet aggregation-inhibiting (antithrombotic) effect of other platelet aggregation inhibitors such as, for example, of P2Y(12) antagonists such as clopidogrel is possible even in samples containing ASA.

The method according to the invention is used most preferably for the determination of the antithrombotic (platelet aggregation inhibitory) effect of a P2Y(12) antagonist, especially for the determination of a P2Y(12) antagonist from the group clopidogrel, ticlopidine, prasugrel (synonym: CS-747) and other thienopyridines, AR-C67085MX (2-propylthio-D-β,γ-dichloromethylene-adenosine 5'-triphosphate), cangrelor (synonym: AR-C69931 MX, N6-[2-methylthio)ethyl]-2-(3, 3,3-trifluoropropyl)thio-5'-adenylic acid), C1330-7 (N1-(6-ethoxy-1,3-benzothiazol-2-yl-2-(7-ethoxy-4-hydroxy-2,2-dioxo-2H-2-6benzo[4,5][1,3]thiazole[2,3-c][1,2,4] thiadiazin-3-yl)-2-oxo-1-ethanesulfonamide), AZD 6140 (nucleoside analog), MRS 2395 (2,2-dimethyl-propionic acid 3-(2-chloro-6-methylaminopurin-9-yl)-2-(2,2-dimethyl-propionyloxymethyl)-propyl ester), and 2-MeSAMP (2-methylthioadenosine 5'-monophospate).

It was also surprisingly found that the method according to the invention can also be used for the determination of the antithrombotic (platelet aggregation inhibitory) effect of a P2Y(1) antagonist. In particular, the method can be used for the determination of the antithrombotic effect of P2Y(1) antagonists from the group MRS 2179 [2'-deoxy-N-6-methyladenosine 3',5'-diphosphate, diammonium salt], MRS 2279 [(N)-methanocarba-N-6-methyl-2-chloro-2'deoxyadenosine 3',5'-bisphosphate], MRS 2500 [2-iodo-N-6-methyl-(N)-methanocarba-2'-deoxyadenosine 3'5'-bisphosphate], A2P5P [adenosine 2',5'-bisphosphate], A3P5P [adenosine 3',5'-bisphosphate], A3P5PS [adenosine 3'-phosphate 5'-phosphosulfate].

The partition member preferably has a circular opening that is produced in the support matrix by punching. The diameter of the opening in the partition member is so dimensioned that a thrombus can form under the conditions of the respective method which closes the opening and can thus stop the blood flow. Preferably the opening in the partition member has a diameter between approximately 100 g/m and approximately 200 µm. Particularly preferably the diameter of the opening in the partition member is about 150 µm.

The following embodiment examples serve to illustrate the method according to the invention and are not to be understood as limiting.

BRIEF DESCRIPTION OF THE DRAWINGS

FIG. 1 shows by way of example how a device which is suitable for carrying out the method according to the invention for the determination of platelet function can be constructed. Shown is a test cartridge in accordance with WO 97/34698 in longitudinal section that is placed in a suitable apparatus for implementing the method according to the invention and into which extends a vacuum apparatus (15) that is responsible for the generation of the partial vacuum.

Figure 1:
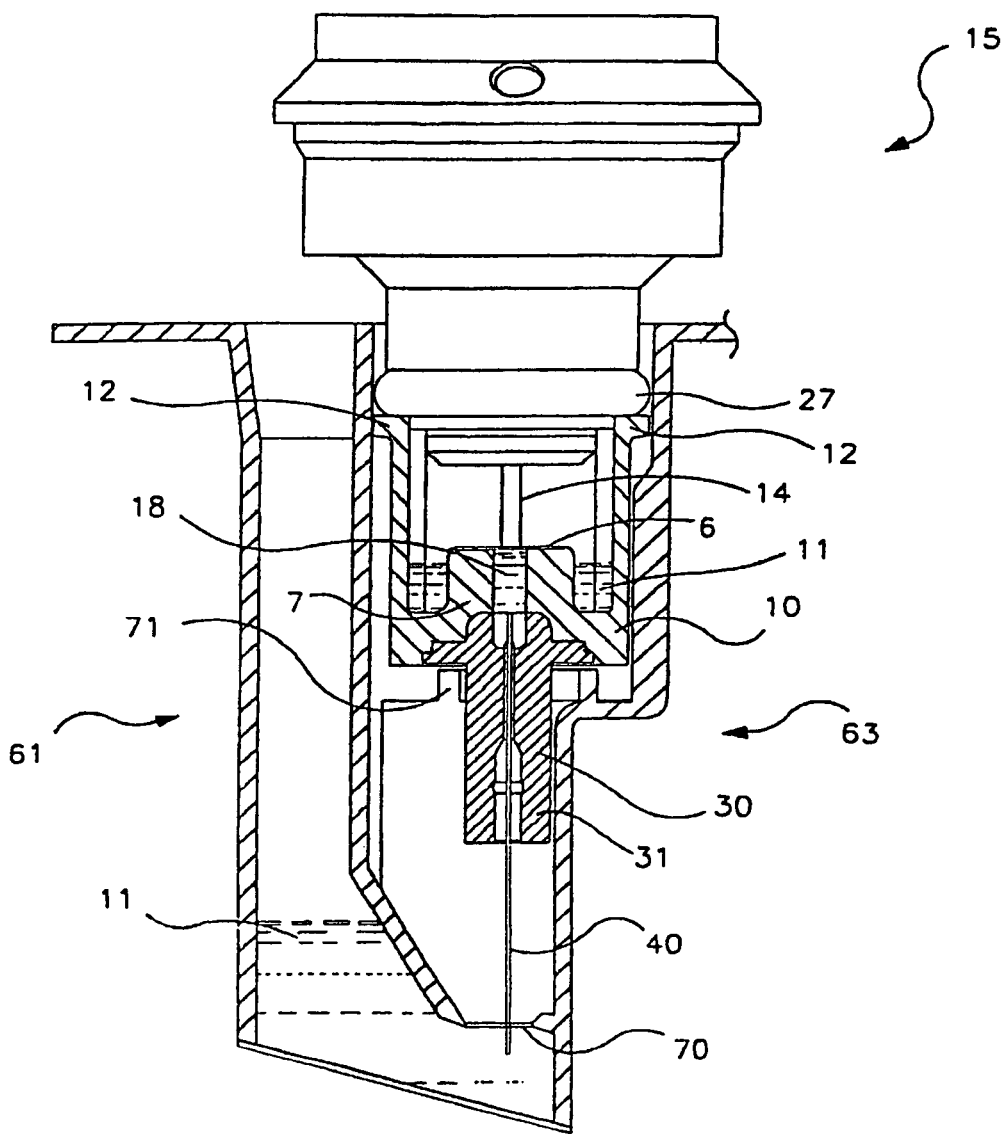
FIG. 1

The vacuum apparatus (15) has a ring gasket (27) which is located as a seal on the circumferential edge (12) of the sample container (10). The test cartridge has a housing that forms a reservoir (61) and a test chamber (63). The test chamber (63) is constructed to accept a sample container (10) the cavity of which can also be referred to as measurement chamber. The sample container (10) supports a partition member (6) coated with reagents with a central opening (aperture) and a capillary attachment (30, 31) that connects the capillary (40) with the sample container (10). Reservoir (61) and test chamber (63) are separated by a penetrable element (70). The figure shows a phase of the test cycle after the vacuum apparatus (15) is in contact with sample container (10) and has moved downwards so that the base of the sample container (10) is in contact with the support (71) and the capillary (40) has penetrated the penetrable element (70) and penetrated into the sample (11). The apparatus produces a partial vacuum in the sample container (10) by means of which the sample (11) is pulled through the capillary (40) into the first compartment (18) of the measurement chamber and then through the opening in the partition member (6).

FIG. 2

Diagram for the illustration of closure times (in seconds [s]) for normal untreated whole blood samples (control) and for whole blood samples that had been treated with the P2Y(12) antagonist MRS 2395 or the COX-1 inhibitor acetylsalicylic acid (ASA) in vitro (see Example 1). Whole blood samples from 11 healthy donors anticoagulated with buffered sodium citrate were used. The means and standard deviations of the closure times measured with Col/Epi test cartridges (cut-off: 158 seconds) are shown. The left-hand block shows the closure times for samples which, in accordance with the prior art, were not mixed with an activator of intracellular adenylate cyclases (untreated). The closure times of samples mixed according to the invention with PGE1 or with forskolin before passing through the capillary are shown in the middle and right-hand block.

FIG. 3

Diagram for illustration of the closure times (in seconds [s]) for normal untreated whole blood samples (control) and for whole blood samples treated in vitro with the P2Y(12) antagonist MRS 2395 or the COX-1 inhibitor acetylsalicylic acid (ASA) (see example 1). Whole blood samples from 11 healthy donors anticoagulated with buffered sodium citrate were used. The means and standard deviations of the closure times measured with Col/ADP test cartridges (cut-off: 115 seconds) are shown. The left-hand block shows the closure times for samples which, in accordance with the prior art, were not mixed with an activator of intracellular adenylate cyclases (untreated). The closure times of samples mixed according to the invention with PGE1 or with forskolin before passing through the capillary are shown in the middle and right-hand block.

EXAMPLES

Example 1

Use of the Method According to the Invention for the Determination of the Antithrombotic Effect of a P2Y(12) Antagonist and of Acetylsalicylic Acid In Vitro Using the Standard Test Cartridges Col/Epi and Col/ADP 1a) Sample Preparation Venous blood was taken from 11 healthy donors and anticoagulated with sodium citrate (3.2% buffered Na citrate).

Aliquots of the citrated whole blood sample were treated in vitro with the P2Y(12) antagonist MRS 2395 (Sigma-Aldrich Chemie GmbH, Steinheim, Germany). For this purpose an ethanolic MRS 2395 stock solution (15 mg/mL) was mixed with the whole blood samples so that an end concentration of 100 μmol/L was obtained.

Further aliquots of the citrated whole blood samples were treated in vitro with the COX-1 inhibitor acetylsalicylic acid (abbr.: ASA; Sigma-Aldrich Chemie GmbH, Steinheim, Germany). For this purpose an aqueous ASA stock solution (1 mg/mL) was mixed with whole blood samples so that an end concentration of 30 μmol/L was obtained.

After addition of the reagents the blood samples were incubated at room temperature for 5 minutes.

1b) Determination of the Antithrombotic Effect of MRS 2395 by ADP Induced Light Transmission Aggregometry (According to Born)

In order to check whether the samples treated with MRS 2395 actually show a reduced platelet aggregation, platelet rich (PRP) and platelet poor (PPP) plasma was prepared from aliquots of the untreated and MRS 2395-treated whole blood samples described under Example 1a). Then the samples were treated with 5 μM ADP. The PPP samples were used as blank controls. The photometric measurement of the aggregation reaction was carried out in the automated coagulation apparatus BCT® (Dade Behring Marburg GmbH, Marburg, Germany) under continuous stirring (600 rpm). The platelet aggregation of the samples treated with MRS 2395 was reduced by a mean of 27% compared with the platelet aggregation of the untreated samples.

1c) Determination of the Reference Range for Col/Epi and Col/ADP Test Cartridges Venous blood was taken from healthy donors and anticoagulated with sodium citrate (3.2% buffered Na citrate). The closure time determination was carried out for each whole blood sample in the PFA-100® apparatus. Samples from 186 donors were determined in duplicate with a Col/Epi PFA-100® test cartridge [see Example 1d)] and a Col/ADP PFA-100® test cartridge [see Example 1d)].

The reference ranges (normal range) for the Col/Epi closure time and the Col/ADP closure time were established in that the measurement value ranges determined in which 90% of the measurement values for the healthy subjects were found (90% central interval of the normal distribution of all measurements). This gave the following reference ranges for the closure times:

| Col/Epi | 70–158 seconds |
|---|---|
| Col/ADP | 60–115 seconds. |

The upper reference limit of the reference range was defined as cut-off, i.e. as threshold value, for a platelet dysfunction. If the closure time of a patient sample deviates from the reference range it can indicate a platelet dysfunction. This means Col/Epi closure times that are greater than 158 seconds and Col/ADP closure times that are greater than 115 seconds indicate the presence of a platelet dysfunction within the sense of a reduced aggregation efficiency.

1d) Determination of the Antithrombotic Effect of MRS 2395 and Acetylsalicylic Acid Using the Method According to the Invention Under Flow Conditions To determine the closure time using a Col/Epi PFA-100® test cartridge (2 μg of collagen and 10 μg of epinephrine on the partition member; 150 μm aperture diameter; Dade Behring Marburg GmbH, Marburg, Germany) and using a Col/ADP PFA-100® test cartridge (2 μg of collagen and 50 μg of ADP on the partition member; 150 μm aperture diameter; Dade Behring Marburg GmbH, Marburg, Germany) as measure of platelet function, whole blood samples described in Example 1a) were investigated in a PFA-100® apparatus (Platelet Function Analyzer-100, Dade Behring Marburg GmbH, Marburg, Germany).

Aliquots of the samples described in 1a) were taken and mixed according to the invention either with prostaglandin E1 (abbr.: PGE1) or with forskolin (both purchased from Sigma-Aldrich Chemie GmbH, Steinheim, Germany) for activating intracellular adenylate cyclases. For this purpose, the samples were mixed with an ethanolic PGE1 stock solution (0.05 mg/mL) or with an ethanolic forskolin stock solution (5 mg/mL) to reach a final concentration of 12.5 nM PGE1 or a final concentration of 1 µM forskolin. Further aliquots of the samples described in 1a) were not mixed with an activator of intracellular adenylate cyclases and served as control.

Then in each case 800 µl of the blood samples mixed with PGE1 or forskolin, or of the control samples were put into the reservoir of a Col/Epi or Col/ADP test cartridge (+37° C.) and incubated in the apparatus at +37° C. for 3 minutes. A partial vacuum of −40 mbar was generated by the apparatus, thus sucking the blood out of the reservoir through the capillary (diameter 200 µm) and finally through the opening (aperture) of the partition member into the measurement chamber. The closure time was determined as the time required until the aperture was closed by formation of a blood clot. Each of the investigated samples was determined in duplicate, and the mean of a duplicate determination was used as measured value.

Figure 2:
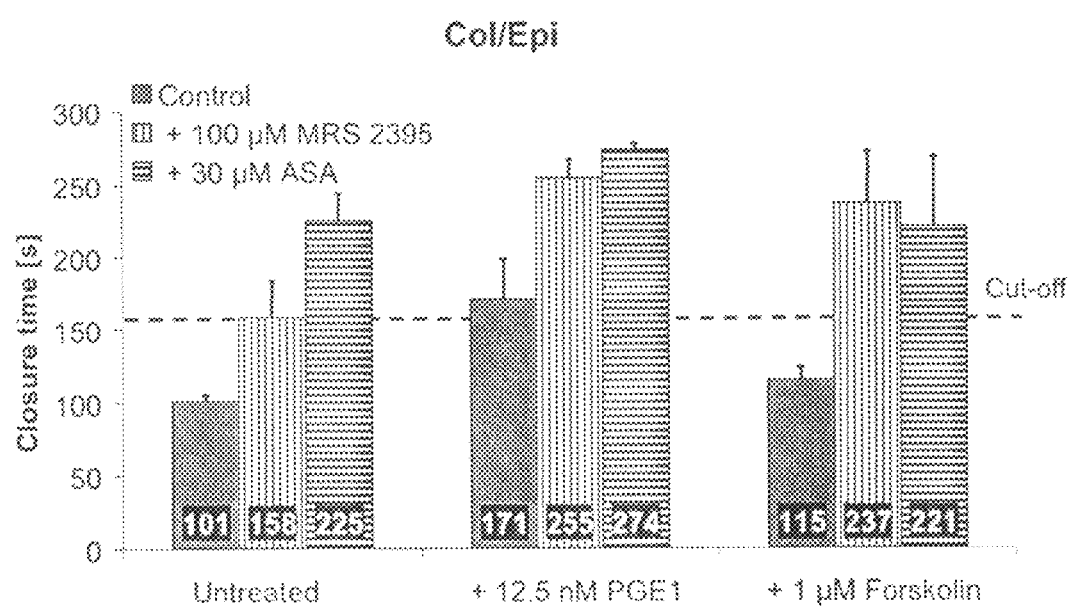
Figure 3:
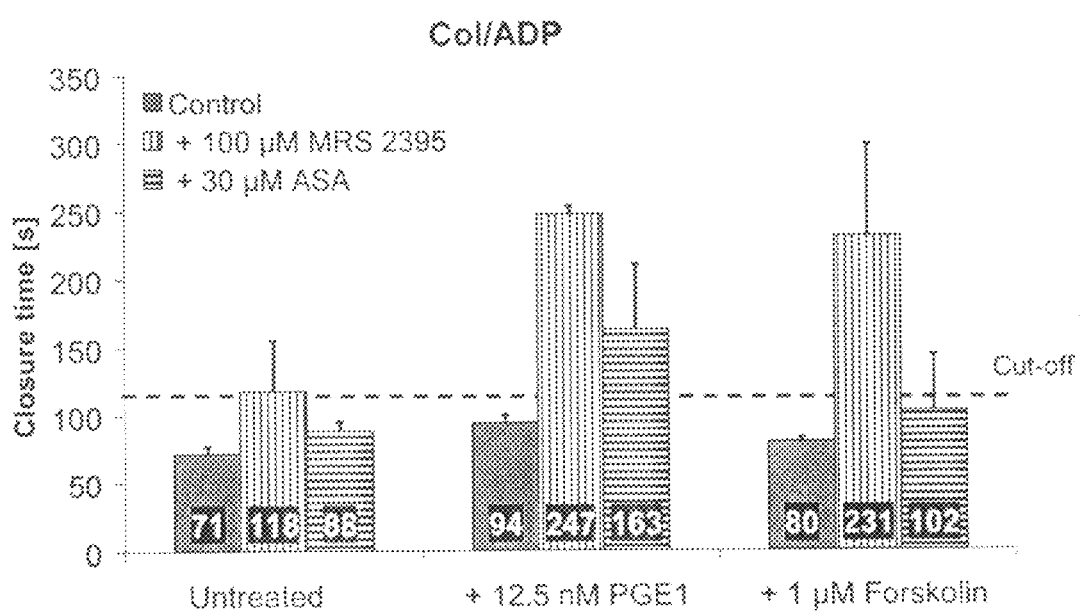

The results of the investigations are summarized in FIG. 2 for the Col/Epi test cartridge and in FIG. 3 for the Col/ADP test cartridge in conjunction with the relevant descriptions of the figures.

Table 1 and Table 2 give details of how many of the in each case 11 MRS 2395- or acetylsalicylic acid-treated samples had a closure time above the cut-off measured with the aid of the method according to the invention using a conventional Col/Epi test cartridge (Table 1) or Col/ADP test cartridge (Table 2).

Col/Epi Test Cartridge

Using the Col/Epi test cartridge, an abnormally reduced platelet aggregation was measured without addition of an activator of intracellular adenylate cyclases (control) in only 3 of 11 MRS 2395-treated samples and in 8 of 11 ASA-treated samples. An abnormally reduced platelet aggregation is detected by use of the method according to the invention, i.e. by previous mixing of the samples with PGE1 or forskolin, in all MRS 2395- and all ASA-treated samples on use of PGE1, and in 9 of 11 MRS 2395-treated samples and in all ASA-treated samples on use of forskolin. However, the amount of prostaglandin E1 used also leads to a significant prolongation of the closure times of the controls, whereas only a slight prolongation of the closure times of the controls is to be observed with the amount of forskolin used. Use of the method according to the invention leads to a distinct increase in the sensitivity of the Col/Epi test cartridge for a platelet dysfunction caused by blocking of the P2Y(12) receptor or by inhibition of cyclooxygenase-1.

| Activator | Col/Epi test cartridge Number of samples with closure times above the cut-off (n = 11) Sample | |
|---|---|---|
| | MRS 2395 (P2Y(12) antagonist) | Acetylsalicylic acid (COX-1 inhibitor) |
| Control | 3 | 8 |
| +12.5 nM PGE1 | 11 | 11 |
| +1 µM forskolin | 9 | 11 |

Col/ADP Test Cartridge

Using the Col/ADP test cartridge, an abnormally reduced platelet aggregation was measured without addition of an activator of intracellular adenylate cyclases (control) in only 2 of 11 MRS 2395-treated samples and in only 1 of 11 ASA-treated samples. An abnormally reduced platelet aggregation was detected by use of the method according to the invention, i.e. by previous mixing of the samples with PGE1 or forskolin, in all MRS 2395-treated samples and in 4 of 11 ASA-treated samples on use of PGE1, and in 10 of 11 MRS 2395-treated samples and in none of the ASA-treated samples on use of forskolin. Neither the amount of forskolin used nor the amount of prostaglandin E1 used led to a significant prolongation of the closure times of the controls. The sensitivity for blocking of the P2Y(12) receptor can be distinctly increased by adding 1 µM forskolin, without thereby causing a significant sensitivity for the ASA-induced platelet dysfunction, as is the case on addition of 12.5 nM prostaglandin.

The method according to the invention is thus suitable for differentiating the two classes of antithrombotics, because of its high sensitivity for P2Y(12) antagonist-induced platelet dysfunctions and, in the case of the Col/ADP test cartridge, its low sensitivity for acetylsalicylic acid-induced platelet dysfunctions.

TABLE 2

| Activator | Col/ADP test cartridge Number of samples with closure times above the cut-off (n = 11) Sample | |
|---|---|---|
| | MRS 2395 (P2Y(12) antagonist) | Acetylsalicylic acid (COX-1 inhibitor) |
| Control | 2 | 1 |
| +12.5 nM PGE1 | 11 | 4 |
| +1 µM forskolin | 10 | 0 |

The invention claimed is:

1. A method for the determination of an antithrombotic effect of a P2Y(12) antagonist or a P2Y(1) antagonist in a whole blood sample, the method comprising the following steps:
   a) passing the blood through a capillary and then through an opening of a partition member which comprises at least one platelet activator from the group of purinergic receptor activators and which further comprises collagen; and
   b) measuring the time that is required for the formation of a thrombus at the opening of the partition member up to closure of the opening;
   wherein the whole blood sample is mixed with forskolin in a final concentration of from 0.1 to 5 µM before passing through the capillary,
   wherein the whole blood sample comprises one or more of the P2Y(12) antagonist and the P2Y(1) antagonist, and optionally an acetylsalicylic acid, and
   wherein the time measured in step (b) indicates the antithrombotic effect of the P2Y(12) antagonist or the P2Y(1) antagonist in the whole blood sample, and wherein the time measured in step (b) does not indicate the antithrombotic effect of the acetylsalicylic acid in the whole blood sample.

2. The method as claimed in claim 1, wherein the partition member used in step a) comprises at least one purinergic receptor activator from the group adenosine 5'-diphosphate, 2-methylthioadenosine 5'-diphosphate, and their derivatives.

3. The method as claimed in claim 1, wherein the whole blood sample is anticoagulated with citrate, a direct thrombin inhibitor, or a direct factor Xa inhibitor.

4. The method as claimed in claim 1, wherein the P2Y(12) antagonist is selected from clopidogrel, ticlopidine, prasugrel, MRS 2395, AR-C67085MX, cangrelor, C1330-7, and 2-methylthioadenosine 5'-monophosphate.

5. The method as claimed in claim 1, wherein the P2Y(1) antagonist is selected from MRS 2179, MRS 2279, MRS 2500, adenosine 2',5'-bisphosphate, adenosine 3',5'-bisphosphate, and adenosine 3'-phosphate 5'-phosphosulfate.

6. The method as claimed in claim 1, wherein forskolin is added in a final concentration of from 0.5 to 2.5 µM to the whole blood sample.

7. The method as claimed in claim 1, wherein forskolin is added in a final concentration of from 1.0 to 1.5 µM to the whole blood sample.

* * * * *